(12) United States Patent
Bryan et al.

(10) Patent No.: US 10,327,962 B2
(45) Date of Patent: Jun. 25, 2019

(54) CLOTH DIAPER WITH ADJUSTMENT FEATURES

(71) Applicant: Dorothy E. Bryan, Xinjiang (CN)

(72) Inventors: Dorothy E. Bryan, Xinjiang (CN); Laural R. Bryan, Co. Cork (IE)

(73) Assignee: Nua Baby Limited, Dunmanway, County Cork (IE)

( * ) Notice: Subject to any disclaimer, the term of this patent is extended or adjusted under 35 U.S.C. 154(b) by 592 days.

(21) Appl. No.: 14/776,247

(22) PCT Filed: Mar. 14, 2014

(86) PCT No.: PCT/IB2014/059840
§ 371 (c)(1),
(2) Date: Sep. 14, 2015

(87) PCT Pub. No.: WO2014/141203
PCT Pub. Date: Sep. 18, 2014

(65) Prior Publication Data
US 2016/0143789 A1    May 26, 2016

Related U.S. Application Data

(60) Provisional application No. 61/794,851, filed on Mar. 15, 2013.

(51) Int. Cl.
*A61F 13/15*    (2006.01)
*A61F 13/493*    (2006.01)
(Continued)

(52) U.S. Cl.
CPC ...... *A61F 13/493* (2013.01); *A61F 13/15268* (2013.01); *A61F 13/49003* (2013.01);
(Continued)

(58) Field of Classification Search
CPC .............. A61F 13/493; A61F 13/15268; A61F 13/49003; A61F 13/49004;
(Continued)

(56) References Cited

U.S. PATENT DOCUMENTS 1,833,960 A    12/1931    Alsop
1,977,604 A    10/1934    Alsop
(Continued)

FOREIGN PATENT DOCUMENTS

FR    2762507 A1    10/1998
GB    2468724 A    9/2010

OTHER PUBLICATIONS

PCT International Search Report dated Dec. 12, 2014 for International Application No. PCT/IB2014/059840, from which the instant application is based, 3 pgs.

*Primary Examiner* — Jacqueline F Stephens
(74) *Attorney, Agent, or Firm* — Fredrikson & Byron, P.A.

(57) ABSTRACT

This disclosure provides systems and methods for an adjustable reusable diaper. Some systems include a reusable diaper including a sealing apparatus configured keep fluid sealed within the diaper. The sealing apparatus may include one or more elastic members and one or more gussets where one elastic member is threaded through channels of the one or more gussets. Some systems include a reusable diaper and one or more soaker pads configured to be attachable to the reusable diaper. The soaker pads may be of varying sizes and shapes and can be selectively attached to the reusable diaper to effect different absorption volumes and patterns within the diaper. The soaker pads may be received in one or more pockets of the reusable diaper. Some systems include one or
(Continued)

more openings to a pocket to allow a user to more efficiently attach and position one or more soaker pads in a reusable diaper.

12 Claims, 7 Drawing Sheets

(51) Int. Cl.
    *A61F 13/49*     (2006.01)
    *A61F 13/494*    (2006.01)
    *A61F 13/505*    (2006.01)
    *A61F 13/74*     (2006.01)
    *A61F 13/80*     (2006.01)
    *A61F 13/56*     (2006.01)

(52) U.S. Cl.
    CPC .. *A61F 13/49004* (2013.01); *A61F 13/49413* (2013.01); *A61F 13/505* (2013.01); *A61F 13/74* (2013.01); *A61F 13/80* (2013.01); *A61F 2013/49433* (2013.01); *A61F 2013/5055* (2013.01); *A61F 2013/5683* (2013.01)

(58) Field of Classification Search
    CPC .. A61F 13/49413; A61F 13/505; A61F 13/74; A61F 13/80; A61F 2013/49433; A61F 2013/5055; A61F 2013/5683
    USPC ................................. 604/386, 394, 398, 390
    See application file for complete search history.

(56) References Cited

U.S. PATENT DOCUMENTS

| | | | |
|---|---|---|---|
| 2,134,976 A * | 11/1938 | Lankenau | A41B 13/04 2/265 |
| 2,468,445 A | 4/1949 | Hurst | |
| 2,627,859 A | 2/1953 | Hargrave | |
| 2,632,177 A * | 3/1953 | Bigger | A41B 9/04 2/406 |
| 2,967,526 A | 1/1961 | Olson | |
| 4,816,025 A | 3/1989 | Foreman | |
| 4,850,992 A * | 7/1989 | Amaral | A61F 13/533 604/385.26 |
| 5,239,706 A * | 8/1993 | Stevenson | A41D 1/06 2/400 |
| 5,360,422 A | 11/1994 | Brownlee et al. | |
| 6,579,273 B2 | 6/2003 | Dupuy | |
| 7,575,573 B1 * | 8/2009 | Roe | A61F 13/49011 604/385.27 |
| 7,629,501 B2 | 12/2009 | Labit et al. | |
| 7,914,507 B1 | 3/2011 | Magee | |
| 8,062,276 B2 | 11/2011 | Labit et al. | |
| 8,262,635 B2 | 9/2012 | Labit et al. | |
| 8,398,605 B2 | 3/2013 | Roe et al. | |
| 8,409,163 B2 | 4/2013 | Labit | |
| 8,425,483 B2 | 4/2013 | Ekstrom | |
| 8,430,857 B2 | 4/2013 | Labit et al. | |
| 8,439,887 B1 | 5/2013 | Magee | |
| 8,518,007 B2 | 8/2013 | Labit et al. | |
| 8,591,489 B2 | 11/2013 | Van Bogart | |
| 8,702,669 B2 | 4/2014 | Tournier | |
| D708,319 S | 7/2014 | Labit | |
| D708,320 S | 7/2014 | Labit | |
| D708,739 S | 7/2014 | Labit | |
| 8,777,915 B2 | 7/2014 | Labit et al. | |
| 8,814,843 B2 | 8/2014 | Van Bogart et al. | |
| 8,961,484 B1 | 2/2015 | Ekstrom | |
| 9,572,726 B1 | 2/2017 | Ekstrom | |
| 2009/0216209 A1 | 8/2009 | Ekstrom | |
| 2009/0240228 A1 | 9/2009 | Nonnenmann et al. | |
| 2010/0168709 A1 | 7/2010 | Hodgkin | |
| 2011/0077611 A1 | 3/2011 | Van Bogart | |
| 2011/0137278 A1 | 6/2011 | Ormsby et al. | |
| 2011/0213326 A1 | 9/2011 | Tournier | |
| 2011/0301561 A1 | 12/2011 | Tournier | |
| 2011/0319852 A1 | 12/2011 | Labit | |
| 2012/0010585 A1 | 1/2012 | Labit et al. | |
| 2012/0116340 A1 | 5/2012 | Labit | |
| 2012/0172827 A1 | 7/2012 | Dupuy | |
| 2013/0012903 A1 | 1/2013 | Labit et al. | |
| 2013/0230260 A1 | 9/2013 | Maynard et al. | |

* cited by examiner

SECTION 3-3

SECTION 8-8

CLOTH DIAPER WITH ADJUSTMENT FEATURES

RELATED APPLICATIONS

This application is a 35 U.S.C. 371 national stage filing from International Application No. PCT/IB2014/059840, filed Mar. 14, 2014, which claims priority to U.S. Provisional Patent Application No. 61/794,851, filed Mar. 15, 2013, the teachings of which are incorporated herein by reference.

RELATED APPLICATIONS

This application claims priority to U.S. Provisional Patent Application No. 61/794,851 filed Mar. 15, 2013, the disclosure of which is herein incorporated by reference in its entirety.

BACKGROUND

Diapers, also known as nappies, are a type of underwear that allows for defecation and urination in a discrete manner. Diapers are commonly worn by children who are not yet toilet trained or experience bedwetting. Diapers may also be worn by adults with incontinence, individuals with disabilities, or individuals working under extreme circumstances with limited access to bathrooms.

Cloth diapers are washable diapers that can be used from birth to toilet training. Many modern cloth diapers have soaker pads that are placed inside waterproof diaper shells with snap or hook and loop closures for convenience of use. Cloth diapers can provide for certain advantages over disposable diapers. For example, reusing cloth diapers may reduce household expenses. Also, cloth diapers may provide for health benefits to the wearer of the diaper as some consumers may be concerned with potential toxins and/or chemicals that may be found in the fabrication materials, and/or the methods of manufacture associated with disposable diapers. Cloth diapers can also be more environmentally friendly than disposable diapers as reusing the cloth diapers can significantly reduce landfill waste.

Cloth diapers generally include a sizing system which allows the diaper to be adjustably sized as necessary to fit a wearer of the diaper. The fit of a diaper is of primary concern as ill-fitting diapers can quickly lead to leaking diapers. Many currently available systems are also confusing and may be intimidating and/or discouraging for first-time users.

SUMMARY

Aspects of the present invention are generally directed toward diapers, diaper systems, and methods for using the same. In some embodiments, diapers can include a forward waist portion, a rearward waist portion and an intermediate portion between the forward waist portion and the rearward waist portion. Embodiments can include a scaling apparatus a pair of inner gussets and a pair of outer gussets, each including a channel. The sealing apparatus can include one or more elastic members configured to pass through the channels of each gusset and one or more adjustment mechanisms configured to adjust a tension of the one or more elastic members. Accordingly, the tension in the gussets can be adjusted to conform to the shape of the wearer for enhanced sealing of the diaper against the user.

Some embodiments can include first and second elastic members. For example, the first elastic member can pass through channels of a left inner and a left outer gusset, while the second elastic member passes through channels of a right inner and a right outer gusset. Embodiments can further include either a single or a first and a second adjustment mechanism for adjusting first and second elastic members. Alternative embodiments can include a single elastic member, which can pass through the respective channels of the pair of inner and the pair of outer gussets, for example.

In some examples, a diaper according to the present invention can include exterior and interior panels. A diaper can further include a pocket formed between the exterior and interior panels. The pocket can be accessed via one or more openings. The diaper can include one of more soaker pads releasably attached thereto. In some embodiments, the one or more soaker pads can be inserted into the pocket through the one or more openings. An exemplary diaper can include first and second soaker pads, such that the first and second soaker pads are releasably attached to opposite waist portions of the diaper. In some embodiments, the first and second soaker pads earl overlap in the intermediate portion of the diaper.

Aspects of the present invention can be embodied as a method for using a diaper, including releasably attaching a first soaker pad to the diaper and inserting the first soaker pad into a pocket via a first opening. Various exemplary methods can further include any or all of adjusting the soaker pad within the pocket via a second opening, releasably attaching a second soaker pad to the diaper, inserting the second soaker pad through the second opening, and adjusting the second soaker pad via the first opening. Many configurations and method of using such configurations are possible and contemplated. The details of one or more examples are set forth in the accompanying drawings and the description below. Other features, objects, and advantages will be apparent from the description, drawings, and claims.

BRIEF DESCRIPTION OF THE DRAWINGS

The following drawings are illustrative of particular embodiments of the invention and therefore do not limit the scope of the invention. The drawings are not necessarily to scale (unless so stated) and are intended for use in conjunction with the explanations in the following detailed description. Embodiments of the invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides some practical illustrations for implementing exemplary examples of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives. Directional terms such as top, bottom, lett, right, up, down, over, above, below, beneath, rear, and front, may be used with respect to the drawings. These and similar directional terms are not to be construed as limiting the scope of the disclosure, but rather they are used for purposes of convenience and clarity of the description.

Figure 1:
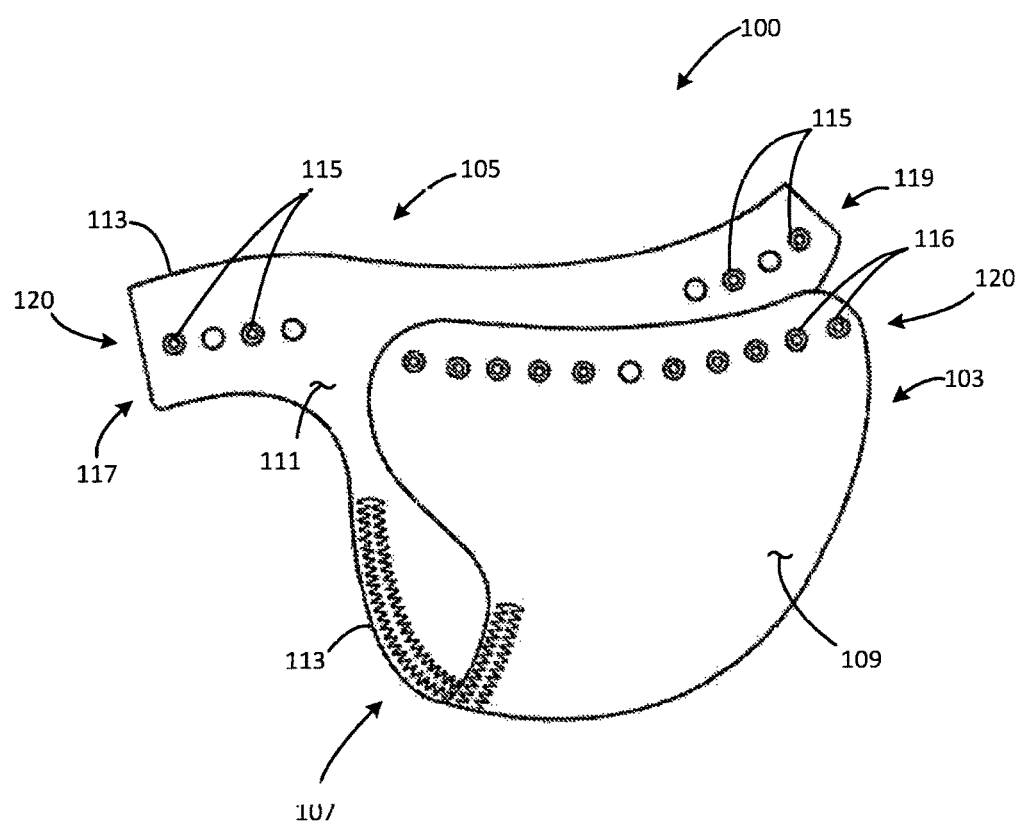
FIG. 1 is a perspective view of a reusable diaper, according to some embodiments.

FIG. 1 is a perspective view of a reusable diaper 100, in accordance with some embodiments. Reusable diaper 100 can have an exterior panel 109 and an interior panel 111 which can be formed from one or more pieces of cloth. In some examples, the exterior panel 109 and interior panel 111 may be formed from two pieces of cloth substantially sewn together about a periphery 113 of the diaper. The exterior panel 109 and the interior panel 111 can form a forward waist portion 103, a rearward waist portion 105, and an intermediate portion 107 that can be intermediate forward waist portion 103 and rearward waist portion 105. According to some examples, intermediate portion 107 can be narrower than forward waist portion 103 and rearward waist portion 105.

According to some examples, the exterior panel 109 can be laminated with a substantially liquid-impervious material. For example, a thermoplastic polyurethane laminate (TPU lamination) can be applied to the fabric, or a polyurethane laminate (PUL) can be used. Other substantially liquid-impervious surface treatments and/or laminates can also be used, as will be apparent to one skilled in the art, and are also considered as being within the intent, scope and spirit of the instant disclosure. In some examples, the exterior panel 109 can be a 100% polyester fabric. In some examples, the exterior panel 109 can be a cotton-polyester blend fabric, a cotton fabric, or a wool fabric. In some examples, the exterior panel 109 can have a velvety or "minky" type feel to the touch. Other materials and/or fabrics can also be used, as will be apparent to one skilled in the art, and are also considered as being within the intent, scope and spirit of the instant disclosure.

In some examples, the interior panel 111 can be a 100% polyester fabric. In some examples, the interior panel 111 can be a cotton-polyester blend fabric, a cotton fabric, a wool fabric, or a fleece. Other materials and/or fabrics can also be used, as will be apparent to one skilled in the art, and are also considered as being within the intent, scope and spirit of the instant disclosure.

In some examples, when reusable diaper 100 is fitted on a wearer, forward waist portion 103 and rearward waist portion 105 may be configured to fit around a front facing portion and a rear facing portion of the wearer's waist, respectively. In such examples, intermediate portion 107 connects forward waist portion 103 and rearward waist portion 105 by passing between the wearer's legs. According to some examples, intermediate portion 107 may be configured to form around the wearer's legs when reusable diaper 100 is worn.

Reusable diaper 100 may be configured to be secured about the waist of a wearer. In some examples, the reusable diaper 100 may include a fastening apparatus 120 including a plurality of releasable fasteners 115 and 116. Fastening apparatus 120 may be disposed on both the forward waist portion 103 and rearward waist portion 105 of the reusable diaper 100. Releasable fasteners 115 can be disposed on side sections 117 and 119 of the rearward waist portion 105 and can be configured to cooperatively connect with releasable fasteners 116 disposed on forward waist portion 103 Side sections 117 and 119 of the reward waist portion 105 may be configured to overlap with the forward waist portion 103 when reusable diaper 100 is worn. The releasable fasteners 115 and 116 may be situated and aligned on side sections 117, 119 and the forward waist portion 103, respectively, so that the releasable fasteners 115 may cooperatively couple with releasable fasteners 116 when side sections 117 and 119 overlap with forward waist portion 103.

Fastening apparatus 120 may comprise one or more types of releasable fasteners. For example, fastening apparatus 120 may include any combination of releasable fasteners including, but not limited, male and female snap fasteners, male and female plastic snap fasteners, hook-and-loop fasteners, and buttons and button holes. Other releasable fasteners and/or releasable fastening techniques, as will be apparent to those skilled in the art, are also considered as being within the intent, scope and spirit of the instant disclosure.

Reusable diaper 100 may also include elastic members to conform the diaper to a shape of a wearer. Elastic members may be incorporated in a number of locations in the diaper to provide, for example, a more comfortable and functional fit and to prevent and/or minimize leaks. For example, elastic members may be incorporated into the forward waist portion 103 and rearward waist portion 105 to conform the diaper to the wearer's waist.

Figure 2:
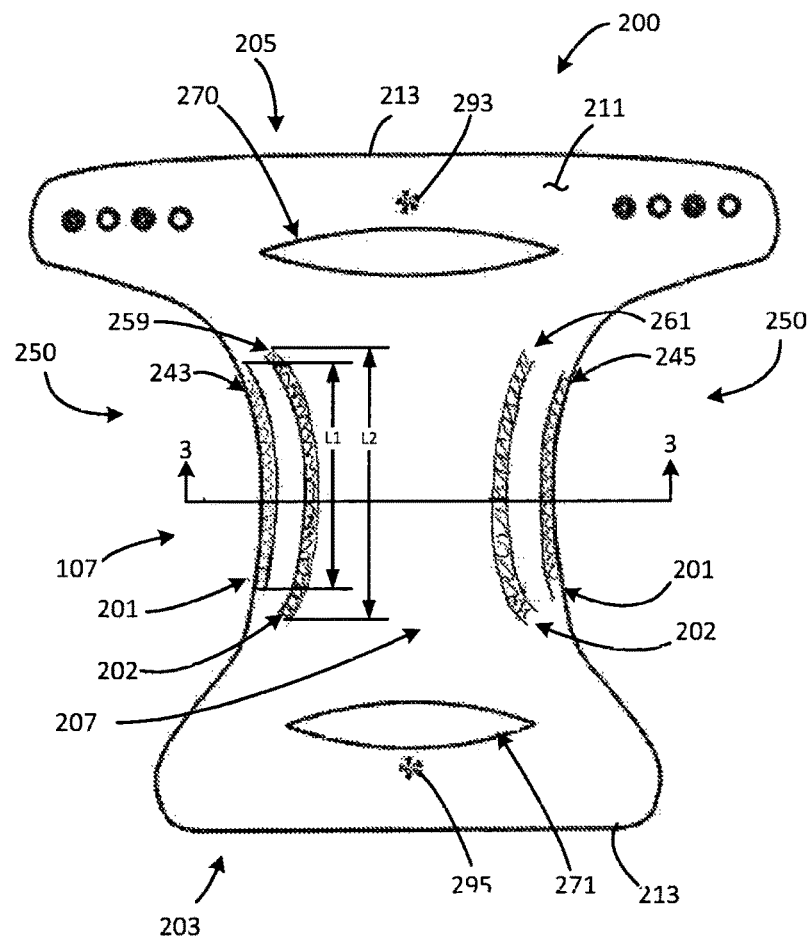
FIG. 2 is a schematic top view of a reusable diaper including a sealing apparatus, according to some embodiments.

According to some examples, a reusable diaper may include a sealing apparatus. FIG. 2 is a schematic top view of an interior panel 211 of reusable diaper 200 including a sealing apparatus 250, according to some examples. In some examples, sealing apparatus 250 may include one or more gussets to form a seal and prevent fluid from within reusable diaper 200 from leaking out of reusable diaper 200. For example, sealing apparatus 250 may include an outer pair of gussets 201 and an inner pair of gussets 202 formed on intermediate portion 207 of reusable diaper 200. The outer pair of gussets may include a left outer gusset 243 and a right outer gusset 245, and the inner pair of gussets may include a left inner gusset 259 and a right inner gusset 261.

In some examples, the length of the outer pair of gussets 201 and the length of the inner pair of gussets 202 may be complimentary to affect comfort for the user and a water-tight seal. For example, inner gussets 259 and 261 can have a length that is longer than outer gussets 243 and 245. One skilled in the art will appreciate that the lengths of the gussets may be configured to suit any particular application. Further, the gussets need not be located exclusively in intermediate portion 207, so the lengths of the gussets may extend the gussets into forward waist portion 103 and/or rearward waist portion 105. According to some examples, outer pair of gussets 201 can be formed along a periphery 213 of reusable diaper 200.

In some examples, the length L1 of outer gussets 243 and 245, as well as the length L2 of the inner gussets 259 and 261, can extend for a short distance, as compared to the length of intermediate portion 207. In some examples, the length L1 of outer gussets 243 and 245 can be longer, for example, extending for the full distance of intermediate portion 207. In some examples, the length L1 of the outer gussets 243 and 245 can have a medium length, for example, where outer gussets 243 and 245 extend for only a section of the length of intermediate portion 207. In some examples, the length L1 of outer gussets 243 and 245 can extend, for example, beyond the length of the intermediate portion 207, and the ends of outer gussets 243 and 245 can be in the forward waist portion 103 and the rearward waist portion 105.

Figure 3:
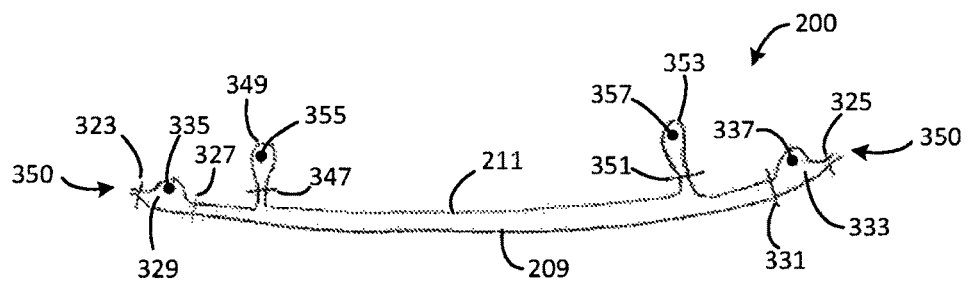
FIG. 3 illustrates a sectional cut taken along line 3-3 of the reusable diaper of FIG. 2.

According to some examples, gussets of a sealing apparatus may be formed in the interior of a diaper to form a water-tight seal around a wearer's legs when worn. For example, FIG. 3 illustrates a sectional cut taken along line 3-3 of reusable diaper 200 of FIG. 2. Each gusset of sealing apparatus 250 may include a channel configured to receive an elastic member. For example, channel 329 can be formed between an interior panel 211 and an exterior panel 209 of reusable diaper 200 using seams 323 and 327. Seam 323 can be created by sewing exterior panel 209 to interior panel 211 along a periphery 350 of reusable diaper 200. Similarly, a second seam 327 can be created by sewing exterior panel 209 to interior panel 211, a short distance inwards of periphery 350. Accordingly, channel 329 can be formed between seams 323 and 327. Similarly, channel 333 can be formed for the right hand side of reusable diaper 200. A seam 325 can be created by sewing exterior panel 209 to interior panel 211 along the periphery 350. A second seam 331 can be created by sewing exterior panel 209 to interior panel 211, a short distance inwards of periphery 350. Accordingly, channel 333 is formed as a result of the two seams 325 and 331.

According to some examples, a channel within a gusset may be created using a single seam. For example, a portion of interior panel 211 can be gathered and a seam 347 can be sewn to form a channel 349. Similarly, a second portion of interior panel 211 can be gathered, and a seam 351 can be sewn to form a channel 353. Generally, a length of each of the channels corresponds to a length of its respective gusset. One skilled in the art will appreciate that the channels may be formed in any suitable manner to suit a specific application.

In some examples, channels 349 and 353 can be located approximately 0.5 inches from periphery 213 of reusable diaper 200. In other examples, channels 349 and 353 can be located between approximately 0.2 to 0.8 inches from periphery 213. In yet other examples, channels 349 and 353 can be located approximately 1.0 inch from periphery 213.

A sealing apparatus of a diaper may include one or more elastic members. According to some examples, a gusset of the sealing apparatus may be configured to receive an elastic member within a channel of the gusset. For example, channel 329 can receive an elastic member 335, and channel 333 can receive an elastic member 337. Similarly, channel 349 can receive an elastic member 355, and channel 353 can receive elastic member 357. When the diaper is worn, tension is applied to elastic members 335, 337, 355, and 357, which causes channels 329, 333, 349, and 353, respectively, to pull away from the surface of the interior panel 211 and closer to the wearer's legs. This feature enables the gussets of each respective channel to provide a snug fit around the legs of a wearer to seal fluids within the diaper. In some examples, the tension of the elastic members can be adjusted to allow the diaper to accommodate wearers of various sizes, or a wearer that grows over time. Adjusting the tension of the elongated elastics is discussed in detail further below.

Figure 4:
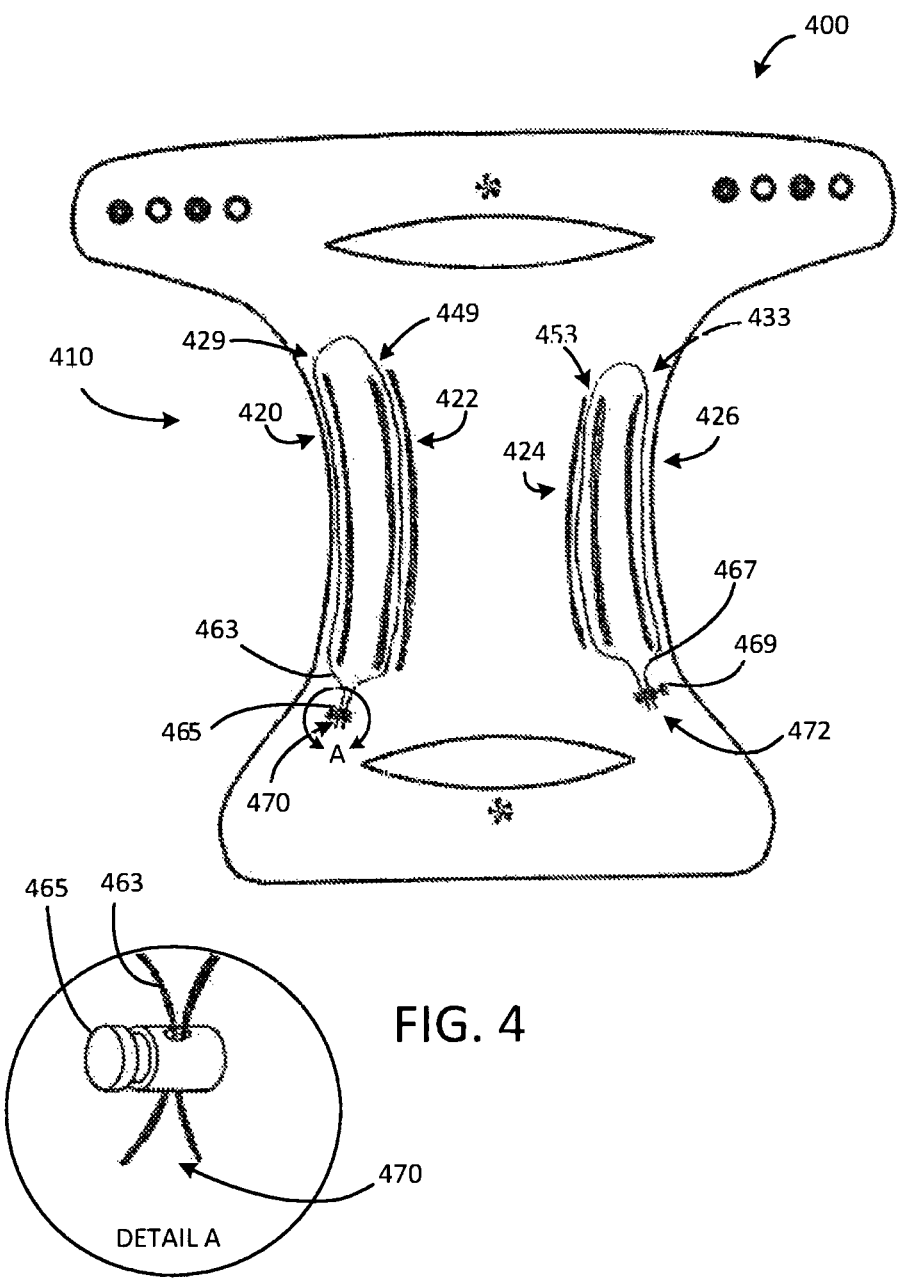
FIG. 4 is a schematic top view of a diaper including a scaling apparatus having two elastic members, according to some embodiments.

FIG. 4 is a schematic top view of a reusable diaper 400 including scaling apparatus 410 having two elastic members 463 and 467. Elastic member 463 is received by channels 429 and 449 of gussets 420 and 422, respectively. Similarly, elastic member 467 is received by channels 433 and 453 of gussets 426 and 424, respectively. In some examples, sealing apparatus 410 may include one or more releasable fasteners to adjust the tension of one or more elastic members. For example, sealing apparatus 410 may include releasable fasteners 465 and 469 which can be configured to adjust the tension of elastic members 463 and 467, respectively, through the gussets. In this example, elastic members 463 and 467 can be tightened by pulling on ends 470 and 472, respectively, to increase the tension applied across the gussets, then readjusting the releasable fasteners to maintain the applied tension. Similarly, the tension of elastic members 463 and 467 can be decreased by releasing releasable fasteners 465 and 469, allowing slack from the ends 470 and 472, respectively, to enter into the gussets, and refastening the fasteners As ran be appreciated, selectively adjusting the tension of elastic members 463 and 467 determines a tension of the gussets and facilitates an adjustment of a fit of reusable diaper 400 around the legs of a wearer.

Figure 5:
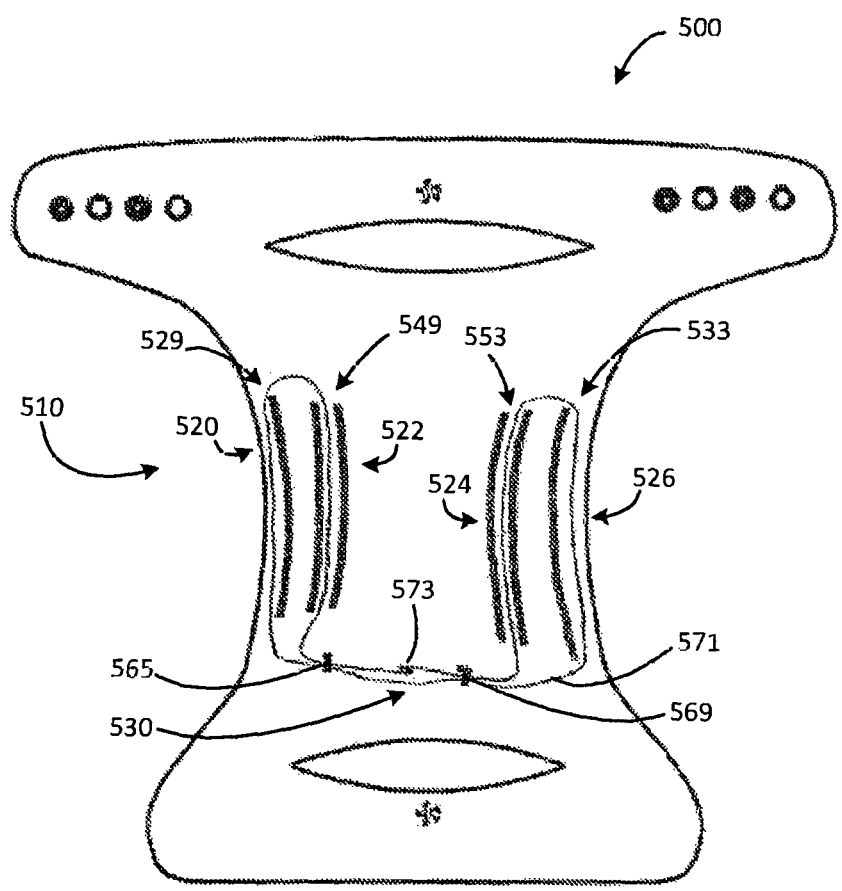
FIG. 5 is a schematic top view of a diaper including a sealing apparatus having one elastic member, according to some embodiments.

According to some examples, a sealing apparatus may include only a single elastic member. For example, FIG. 5 is a diagrammatic illustration of a reusable diaper 500 including a sealing apparatus 510 having one elastic member 571. Elastic member 571 can be routed through channels 529, 549, 553, and 533 of gussets 520, 522, 524, and 526, respectively. In some examples, elastic member 571 can be successively routed through adjacent gussets. Other examples can include different paths of routing elastic member 571 through gussets 520, 522, 524, and 526 such that elastic member 571 applies tension across all the gussets. In this example, elastic member 571 is joined at 573 to form a continuous elastic loop that spans the channels of all the gussets. Accordingly, a user can increase the tension of elastic member 571 through gussets 520, 522, 524, and 526 by pulling on an end 530 of elastic member 571, then adjusting releasable fasteners 565 and 569. Similarly, the tension of elastic member 571 can be decreased by releasing releasable fasteners 565 and 569, allowing slack from end 530 of elastic member 571 to enter into the gussets, then refastening the fasteners. As can be appreciated, selectively adjusting the tension of elastic member 571 determines a tension applied across the gussets and facilitates and adjustment of a fit of reusable diaper 500 around the legs of a wearer.

Sealing apparatus 410 of FIG. 4 and sealing apparatus 510 of FIG. 5 provides for a number of distinct advantages. For example, routing an elastic member through the channels of more than one gusset provides for tension uniformity between the gussets. With reference to FIG. 4, in some examples a tension of elastic member 463 is applied uniformly across gussets 420 and 422, and a tension of elastic member 467 is applied uniformly across gussets 424 and 426. Similarly, with reference to FIG. 5, in some examples the tension of elastic member 471 is applied uniformly across gussets 520, 522, 524, and 526. Applying the tension of an elastic member uniformly across multiple gussets can provide for a more comfortable fit for the wearer.

Routing an elastic member through the channels of more than one gusset also provides the advantage of allowing a user of a diaper to more quickly and efficiently adjust the gussets receiving the elastic member. For example, with reference to FIG. 4, a user can quickly adjust all four gussets 420, 422, 424, and 426 of reusable diaper 400 by only adjusting the tension of two elastic members 463 and 167 and its corresponding releasable fasteners 465 and 469, respectively. Similarly, with reference to FIG. 5, a user can quickly adjust all four gussets 520, 522, 524, and 526 of reusable diaper 500 by only adjusting the single elastic member 471 and its corresponding releasable fasteners 565 and 569, respectively. For example, to increase tension across all four gussets 520, 522, 524, and 526, a user need only to pull on end 530 of elastic member 571 and adjust releasable fasteners 565 and 569. As can be appreciated, adjusting the tension of a single elastic member allows a user to more quickly and efficiently adjust a diaper to fit a shape of a particular wearer compared with having to adjust the tension of each gusset individually.

Other examples include a scaling apparatus having a single elastic member and a single releasable fastener to further increase the case in which a user can adjust a diaper. In such examples the single elastic member can be threaded through the channels of gussets of the diaper such that adjusting the tension of the single elastic member adjusts all the gussets of the diaper. Further, the releasable fastener can be positioned to hold the tension of the elastic member across all the gussets when engaged.

Another advantage to the examples illustrated in FIGS. 4 and 5 are that pairs of gussets can be independently adjusted. For example, with reference to FIG. 4, the tension applied across gussets 420 and 422 is distinct from the tension applied across gussets 424 and 426, as the former is adjusted by elastic member 463 and releasable fastener 465 and the latter is adjusted by elastic member 467 and releasable fastener 469. Similarly, with reference to FIG. 5, in some examples, the tension applied across gussets 520 and 522 is distinct from the tension applied across gussets 524 and 526, as the former is adjusted by the position of releasable fastener 565 and the latter is adjusted by the position of releasable fastener 569.

As discussed above, selectively and/or independently adjusting the tension across the gussets can be advantageous. Diapers typically fit on the legs of a wearer at the upper thigh. For example, infants, babies and toddlers can have a range of weights and body shapes. In addition, each individual infant, baby or toddler can carry their weight in different locations, and at different stages of development their weight and/or body composition may vary. Accordingly, there exists a wide range of sizes for a wearer's upper thighs. Further, the size of the wearer's thighs can change as the wearer grows. Selectively and/or independently adjusting a tension applied across particular gussets of a diaper can be advantageous as it permits a user to tailor the diaper to fit the upper thighs of a particular baby, and adjust the fit according to the baby's changing body composition and/or age. In addition, the fit of the diaper at the upper thigh is not linked to the fit of the diaper at other locations allowing for increased configurability and customization of the diaper to the wearer. This results in a reusable diaper that can be adjusted for a snug fit at the upper thigh independent of other fit adjustments (e.g., the wearer's waist).

Releasable fasteners can include, but are not limited to, cord locks and spring-biased cord locks, including plastic spring-biased cord locks. In some examples, spring-biased releasable fasteners can be used, as shown, for example, in Detail A of FIG. 4. Releasable fasteners can also include toggle fasteners, spring-biased toggle fasteners, spring locks, buttons, and drawstring cord locks (with or without locking wheels). Other releasable fastening devices and/or releasable fastening techniques, as will be apparent to one skilled in the art, are also considered as being within the intent, scope and spirit of the instant disclosure.

Elongated member can include, but is not limited to, elastic cords, fabric elastics, braided elastics, button-hole elastics, and flat elastics (which can include non-roll flat elastics). Other elongated elastics, as will be apparent to one skilled in the art, are also considered as being within the intent, scope and spirit of the instant disclosure.

Figure 6:
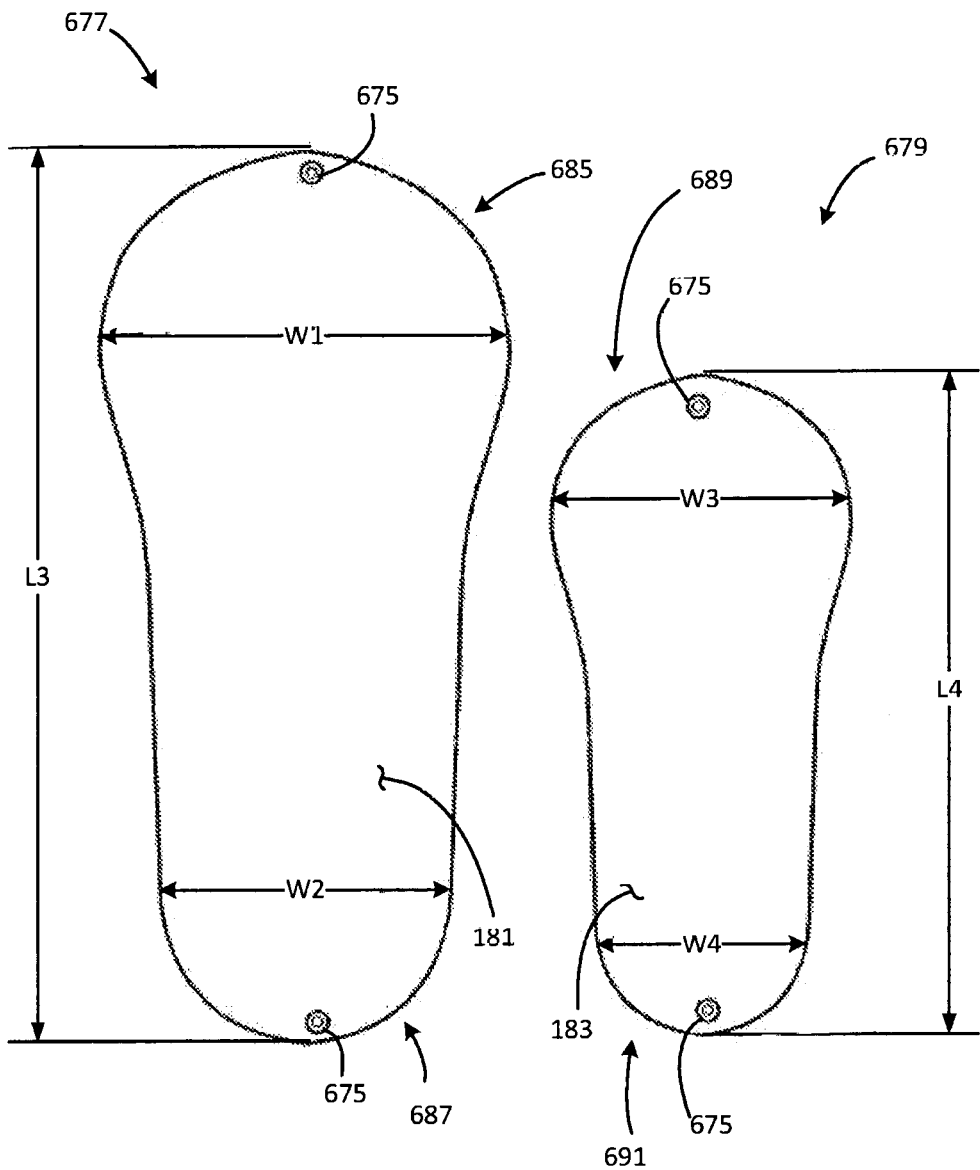
FIG. 6 illustrates soaker pads that can be included in a reusable diaper system, according to some embodiments.

According to some examples, a reusable diaper system can include a reusable diaper and one or more soaker pads. FIG. 6 illustrates soaker pads 677 and 679 that can be included in a reusable diaper system. Soaker pads 677 and 679 can be of any shape and size as to fit within an associated reusable diaper. For example, soaker pads 677 and 679 can be oval shaped, egg shaped, elongated egg shaped, elliptical shaped, key-hole shaped, or any other elongated shape. In this example, soaker pad 677 and 679 are of a similar shape but vary in size. As will be discussed further below, the size of a soaker pad can correlate with a volume of absorption.

According to some examples, soaker pad 677 can have an overall length L3 that is about 11 inches. In some examples, soaker pad 677 can have an overall length L3 that is between about 9 and about 15 inches. In some examples, soaker pad 677 can have an overall length L3 that is between about 10 and about 12 inches. Soaker pad 677 can have a wide end 685 with a width W1 that is about 5.5 inches, and a narrow end 187 with a width W2 that is about 4 inches. In some examples, soaker pad 677 can have a wide end 685 with a width W1 that is between about 3.5 inches and about 5.5 inches, and a narrow end 687 with a width W2 that is between about 2 inches and about 3.5 inches. In some examples, soaker pad 677 can have a wide end 685 with a width W1 that is between about 6 inches and about 8 inches, and a narrow end 687 with a width W2 that is between about 4.5 inches and about 6 inches.

Similarly, according to some examples, soaker pad 679 can have an overall length L4 that is about 9 inches. In some examples, soaker pad 679 can have an overall length L4 that is between about 5 and about 12 inches. In some examples, soaker pad 679 can have an overall length L4 that is between about 7 and about 11 inches. Soaker pad 679 can have a wide end 689 with a width W3 that is about 4.5 inches, and a narrow end 691 with a width W4 that is about 3.5 inches. In some examples, soaker pad 679 can have a wide end 689 with a width W3 that is between about 2.5 inches and about 3.5 inches, and a narrow end 691 with a width W4 that is between about 1.5 inches and about 2.5 inches. In some examples, soaker pad 679 can have a wide end 689 with a width W3 that is between about 5 inches and about 7 inches, and a narrow end 691 with a width W4 that is between about 4 inches and about 5 inches. While specific dimensions of soaker pads 677 and 679 are disclosed above, one skilled in the art will appreciate that the soaker pads may be of any size or shape suitable for a particular purpose.

In some examples, the lower side of the soaker pads can be a microfiber, which can be made of 100% polyester or mixed with polyamide. In some examples, the soaker pads can be stuffed with a material, which can be the same material as is used for the lower side. In some examples, the lower side of the soaker pads can be 80% polyester and 20% polyamide, cotton, organic cotton, bamboo, cotton-bamboo mix, or hemp. Other materials and/or fabrics can also be used, as will be apparent to one skilled in the art, and are also considered as being within the intent, scope and spirit of the instant disclosure.

In some examples, the upper side of the soaker pads can be a 100% polyester fabric. In some examples, the upper side of the soaker pads can be polyester-cotton blend, or cotton. Other materials and/or fabrics can also be used, as will be apparent to one skilled in the art, and are also considered as being within the intent, scope and spirit of the instant disclosure.

In some examples, soaker pad 677 can include one or more attachment points 675. Each attachment point 675 can be configured to be releasably attachable to a corresponding reusable diaper of a reusable diaper system. In some examples, attachment points 675 can include a releasable fastener configured to attach to a corresponding fastener of a reusable diaper. Attachment points 675 can be centered on a vertical axis of symmetry of soaker pads 677 and 679. According to some examples, attachment points 675 can be located at the ends of soaker pads 677 and 679. For example, attachment points can be located within about 1 inch from the edges of the soaker pads. In some examples, the attachment points 175 can be located within in between about 0.25 inches and about 2 inches from the edges of the soaker pads. In some examples, a soaker pad may include a single attachment point positioned on only one end of the soaker pad. Attachment points need not be positioned near an end of a soaker pad. For example, a soaker pad can include an attachment point that is located centrally on the soaker pad. One skilled in the art will appreciate that the particular position of one or more attachment points on a soaker pad can vary depending on a particular application.

As noted above, according to some examples, a reusable diaper system can include a reusable diaper to be used together with one or more soaker pads. In such examples, the reusable diaper can include one or more releasable fasteners corresponding to attachment points or releasable fasteners of one or more soaker pads. For example, FIG. 2 illustrates a reusable diaper that can be used in a reusable diaper system together with one or more soaker pads. With reference to FIG. 2, according to some examples rearward waist portion 205 can have a releasable fastener 293 and/or forward waist portion 203 can have releasable fastener 295, where each respective releasable fasteners can be configured to attach to a soaker pad. With reference to FIGS. 2 and 6, releasable fasteners 293 and 295 can be chosen to work cooperatively with attachment points 675, such that they releasably fasten one to the other. In some examples, releasable fasteners 293 and 295 call be located approximately on the vertical axis of symmetry of the diaper and about 1 inch from periphery 213 of reusable diaper 200. In some examples, releasable fasteners 293 and 295 can be located between about 0.25 inches from periphery 213 of reusable diaper 200 to about 2 inches from periphery 213 of reusable diaper 200. According to some examples, releasable fasteners 293 and 295 can be located on interior panel 211. In some examples, releasable fasteners 293 and 295 can be located on a reinforced portion of interior panel 211, which can be reinforced by sewing a small panel of fabric where the fasteners are to be attached. In some examples, releasable fasteners 293 and 295 can be located on exterior panel 209, near openings 270 and 271 in the interior panel, such that attachment points 675 of soaker pads 677 and/or 679 can be releasably attached to releasable fastener 293 or 295 through the openings. In some examples, releasable fasteners 293 and 295 can be located on a reinforced portion of the exterior panel 209, which can be reinforced by sewing a small panel of fabric where the releasable fastener 293 is to be attached.

Figure 7:
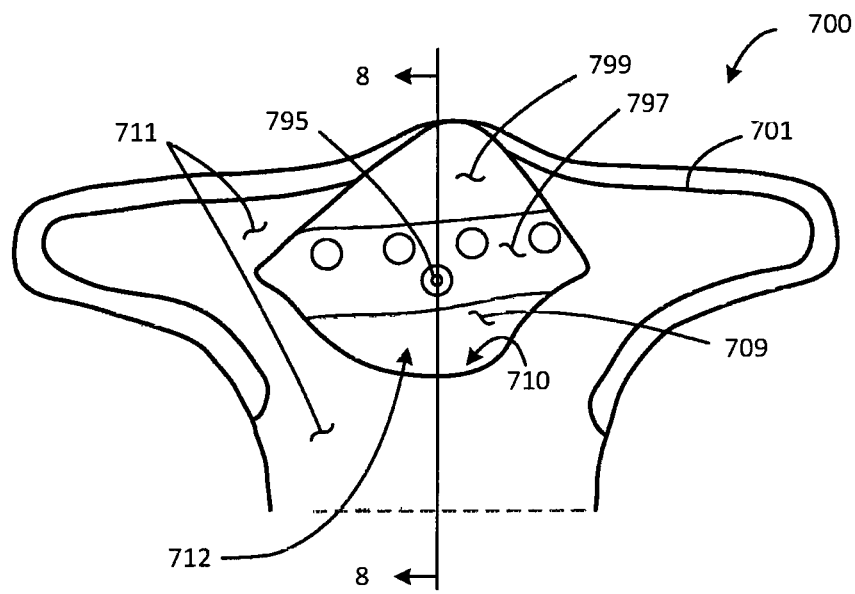
FIG. 7 is a top perspective view of a pocket of reusable diaper, according to some embodiments.

In some examples, a reusable diaper of a reusable diaper system may include one or more pockets configured to receive on or more soaker pads. For example, FIG. 7 is a top perspective view of a pocket 710 of a reusable diaper 700, according to some embodiments. Pocket 710 can be formed between an interior panel 711 and an exterior panel 709 of reusable diaper 700. Accordingly, when one or more soaker pads are received by pocket 710, the soaker pads are positioned to absorb liquids within reusable diaper 700 through interior panel 711. In some examples, soaker pads need not be received within pocket 710 and may sit outside and/or on top of pocket 710.

As noted above, according to some examples reusable diaper 700 may include one or more releasable fasteners 795 configured to fix a position of a soaker pad relative to reusable diaper 700. As can be appreciated, such a feature prevents a soaker pad from shifting while reusable diaper 700 is worn. According to some examples, releasable fastener 795 can be situated within pocket 710 between interior panel 711 and exterior panel 709 of reusable diaper 700.

Figure 8:
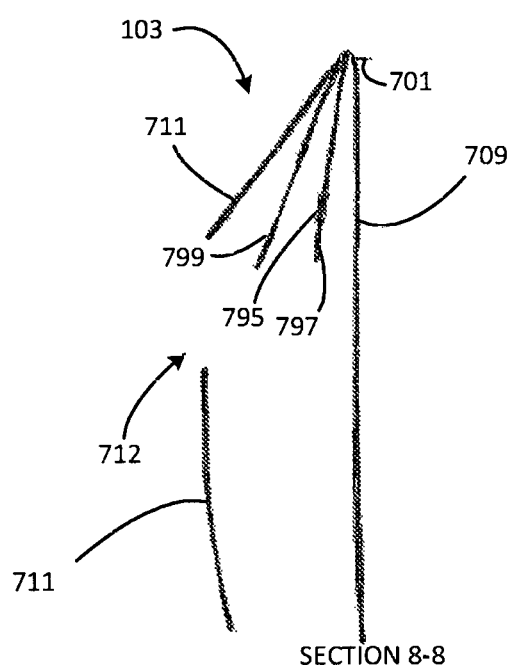
FIG. 8 illustrates a sectional cut taken along line 8-8 of FIG. 7.

In some examples, pocket 710 may include an opening 712 having a flap 799. FIG. 8 is a schematic sectional cut taken along line 8-8 of FIG. 7. The exterior panel 709 can be folded over to create the flap 799. In some examples, flap 799 can comprise a substantially liquid-impervious material to provide additional protection against leaking. Releasable fastener 795 can be attached to an additional reinforcement panel of fabric 797. Seam 701 can be used to fasten all four panels together—the exterior panel 709, the additional reinforcement panel of fabric 797, the flap 799, and the interior lining panel 711. It will be appreciated that, while shown as only traversing a portion of the perimeter of the diaper, scam 701 can be located in any appropriate position and span any appropriate length to effectively fasten the four panels together. As a result, a soaker pad that is attached to releasable fastener 795 can be partially covered by flap 799. This is because a portion of the soaker pad that has been attached to releasable fastener 795 will lie between the additional panel of fabric 797 and the flap 799. Positioning a soaker pad such that a portion of the soaker pad lies beneath the flap 799 provides the advantage of containing any liquid absorbed by an attached soaker pad within pocket 710, thereby preventing any leakage of fluid out of a forward waist portion or up and out of reusable diaper 700 when worn. In some embodiments, the soaker pad can be snapped underneath flap 799, while the rest of the soaker pad can remain outside of the pocket 710. Flap 799 can thus serve to re-direct liquid away from an edge of the reusable diaper 700 to be absorbed by a soaker pad. This feature is particularly advantageous in examples where a substantially liquid-impervious material for the exterior panel material is provided (e.g., flap 799 is comprised of a substantially liquid-impervious material).

Figure 9:
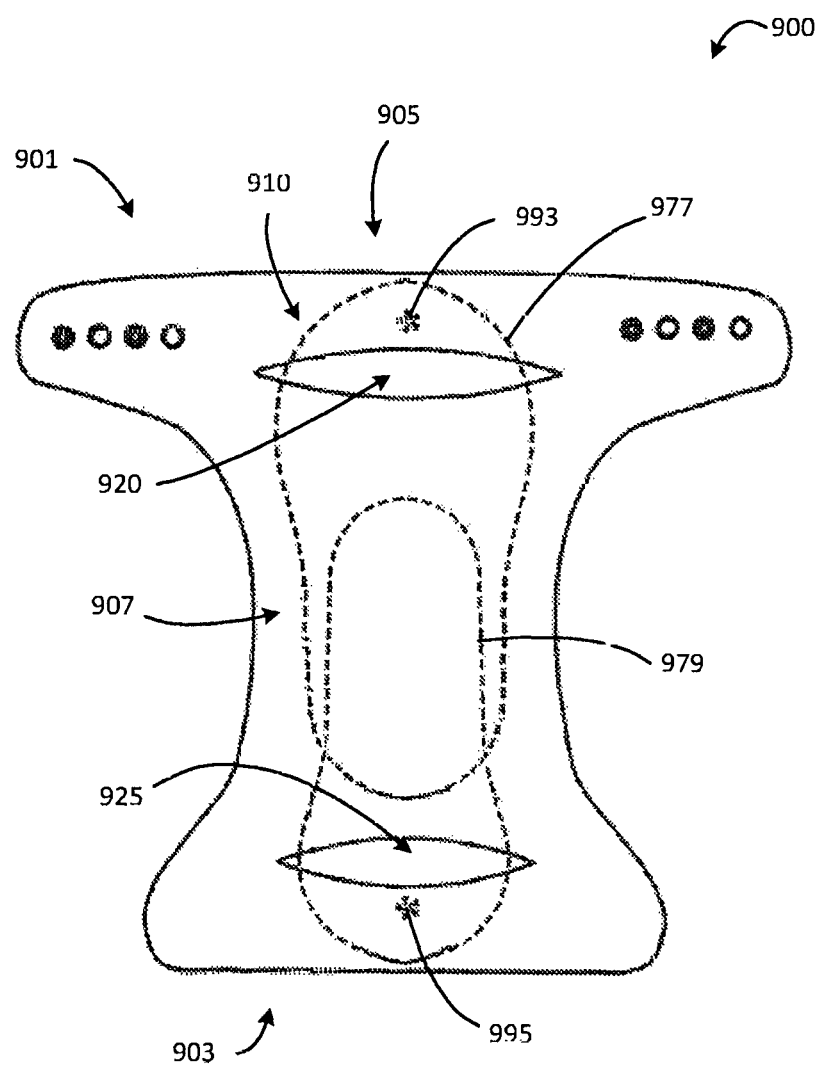
FIG. 9 is a schematic top view of a reusable diaper system including a reusable diaper and soaker pads, according to some embodiments.

In some examples, a reusable diaper system can include a reusable diaper that can be configured to include more than one soaker pad. FIG. 9 is a schematic top view of a reusable diaper system 900 including reusable diaper 901 and soaker pads 977 and 979. In this example, reusable diaper 901 is configured to receive soaker pads 977 and 979. Soaker pads 977 and 979 are represented by broken lines and are received within pocket 910 and are attached to reusable diaper 901 via releasable fasteners 993 and 995, respectively. In this example, soaker pad 977 is attached to reusable diaper 901 at rearward waist portion 905 while soaker pad 979 is attached to reusable diaper 901 at forward waist portion 903.

Reusable diapers that can include more than one soaker pad to provide the advantage of increasing a volume of fluid reusable diaper 901 can absorb.

According to some examples, a reusable diaper system can include a reusable diaper that can be configured to receive one or more soaker pads of varying sizes. As shown in FIG. 9, reusable diaper 901 of reusable diaper system 900 is configured to receive soaker pads 977 and 979, which differ in size. This feature can provide for cost and material savings. As a simple example, if soaker pad 979 can absorb one ounce of fluid and soaker pad 977 can absorb two ounces of fluid, reusable diaper system 900 can be configured to absorb one ounce by using only soaker pad 979, two ounces by using only soaker pad 977, and three ounces by using both soaker pads 977 and 979. In comparison, a user using a reusable diaper system that includes a reusable diaper configured to receive only one soaker pad must acquire three soaker pads to achieve comparable results: a one ounce soaker pad, a two ounce soaker pad, and a three ounce soaker pad. This feature is particularly advantageous for reusable diapers that are used together with an infant as they grow, as the amount of absorption required of the reusable diaper increases over time as the child grows older.

According to some examples, a reusable diaper system can include an overlapping soaker pad feature. More specifically, a reusable diaper of the system is configured to receive more than one soaker pad in such a way that the soaker pads overlap. For example, FIG. 9 illustrates soaker pad 977 and 979 overlapping within pocket 910 of reusable diaper 901. As a result of the size and shape of soaker pads 977 and 979, a tailored location of extra absorbency can be achieved, which can include the location of an overlap. Such flexibility may be desired so that a user can tailor the location of the absorbency according to a number of factors. Such factors can include, for example, the activity level of a wearer, the gender (boy/girl) of the wearer and/or a past pattern of soiling a diaper. As just one example, a user may choose to overlap soaker pads near a forward waist portion of a diaper where a higher volume of fluid is more likely due to urination. Conversely, a user may choose not to overlap soaker pads near an area of a diaper where there will be a low volume of fluid, thereby providing the advantage of less bulk to the diaper. In some examples, the soaker pads can overlap near a middle of an intermediate portion of a diaper to offer more fluid absorption where fluid tends to matriculate and/or pool in the reusable diaper. One skilled in the art can appreciate that any combination of soaker pads of different or identical sizes can be used to effect a desirable overlap and absorption pattern. For example, contemplated embodiments also include using two small soaker pads 979 in a diaper; as well as using two large soaker pads 977 in a diaper.

Additionally, various sizes of soaker pads can be used to facilitate changing size of the wearer. For example, one or more small soaker pads 979 can be used in a diaper for a newborn. As the child grows, at least one of the small soaker pads 979 can be replaced with a large soaker pad 977. Generally, as a child grows, greater absorption may be required of the diaper. Accordingly, larger or additional soaker pads can be used in the diaper to enhance absorption while the physical size of the diaper can be adjusted to accommodate the growing wearer.

According to some examples, a pocket can include more than one opening to facilitate attaching one or more soaker pads to a reusable diaper. According to some examples, pocket 910 can include two openings 920 and 925 positioned near rearward waist portion 905 and forward waist portion 903, respectively. In other examples, openings may also be positioned in an intermediate portion 907 of reusable diaper 901. Openings 920 and 925 can be centered on a vertical axis of symmetry of reusable diaper 901. Openings 920 and 925 can be any size to accommodate soaker pads to be used in reusable diaper system 900. For example, openings 920 and 925 may be sized to allow soaker pads 977 and/or 979 to lie flat within the openings without bunching up.

A number of advantages are associated with providing multiple openings to a pocket of a reusable diaper. For example, multiple openings allow a user to more efficiently attach and position a single soaker pad to a reusable diaper. For example, a user can use openings 920 and 925 to attach soaker pad 977 to reusable diaper 901 by first attaching soaker pad 977 to releasable fastener 993 then inserting or "stuffing" the soaker pad into opening 920. It can be appreciated, however, that depending on the size of opening 920 and the size of the user's hand, it may be difficult to insert the soaker pad 977 to lay flat within pocket 910. Stuffing soaker pad 977 into pocket 910 using only opening 920 may result in bunching of soaker pad 977 within pocket 910. Such bunching of a soaker pad creates a non-uniform distribution and an undesirable absorption pattern in the reusable diaper. To position soaker pad 977, a user may access pocket 910 via opening 925 and pull the soaker pad 977 the remainder of the way across reusable diaper 901. Further, a user may use opening 925 to adjust the position of soaker pad 977 within pocket 910, for example to center soaker pad 977 along a central axis of reusable diaper 901. Thus, the additional access provided by multiple openings can help a user insert and position a soaker pad within a pocket. This usage of a multiple openings feature of a reusable diaper system is particularly advantageous when attaching larger soaker pads that are hard to insert across the length of the diaper. In some examples, a soaker pad can be further secured within a pocket using more than one releasable fastener. For example, once soaker pad 977 is positioned within pocket 910, the position of soaker pad 977 can be further secured by additionally attaching soaker pad 977 to releasable fastener 995. Also, as noted above, a soaker can be positioned within a reusable diaper with multiple releasable fasteners without being received in a pocket. For example, soaker pad 977 can be attached to releasable fasteners 993 and 995, underneath one or more flaps on the front or back of the diaper for example, to secure its position within reusable diaper 901 while it lies outside of pocket 910 on top of the reusable diaper.

A number of advantages are also provided when using the multiple openings feature in connection with an overlapping soaker pad feature. For example, the positioning of opening 920 and 925 in reusable diaper 901 allows for different locations in which to attach soaker pads (e.g., releasable fasteners 993 and 995). As can be appreciated, the position of openings 920 and 925 can then help determine an overlap pattern, and therefore an absorption pattern, for soaker pads 977 and 979. One skilled in the art will appreciate that these two features can be used in tandem to provide many different overlap patterns to effect different absorption patterns as necessary for a particular application.

In the foregoing detailed description, the invention has been described with reference to specific embodiments. However, it may be appreciated that various modifications and changes can be made without departing from the scope of the invention as set forth in the appended claims.

The invention claimed is:

1. A diaper comprising:
   a forward waist portion;
   a rearward waist portion;
   an intermediate portion between the forward waist portion and the rearward waist portion;
   a sealing apparatus including
      a pair of inner gussets each including a channel,
      a pair of outer gussets each including a channel and being formed along a periphery of the intermediate portion of the diaper,
      a first elastic member passing through the respective channels of a first inner gusset of the pair of inner gussets and a first outer gusset of the pair of outer gussets,
      a second elastic member passing through the respective channels of a second inner gusset of the pair of inner gussets and a second outer gusset of the pair of outer gussets, and
      one or more adjustment mechanisms configured to adjust a tension of the first and second elastic members.

2. The diaper of claim 1, wherein the sealing apparatus includes a single elastic member, the single elastic member including the first and second elastic members, such that the single elastic member passes through the respective channels of the pair of inner gussets and the pair of outer gussets.

3. The diaper of claim 2, wherein the sealing apparatus includes a single adjustment mechanism configured to adjust the tension of the single elastic member.

4. The diaper of claim 2, wherein the sealing apparatus includes a first adjustment mechanism and a second adjustment mechanism, the first adjustment mechanism configured to adjust the tension of the single elastic member received in the first inner gusset and the first outer and the second adjustment mechanism configured to adjust the tension of the single elastic member received in the second inner and the second outer gusset.

5. The diaper of claim 1, wherein the one or more adjustment mechanisms is configured to adjusting a fit of the diaper around the legs of the wearer when the diaper is worn.

6. The diaper of claim 1, wherein each of the gussets in the pair of outer gussets extends beyond the length of the intermediate portion.

7. The diaper of claim 1, wherein the intermediate portion is configured to form around a wearer's legs when the diaper is worn, and wherein the first inner gusset and the first outer gusset fit around a first leg of a wearer and the second inner gusset and the second outer gusset fit around a second leg of a wearer when the diaper is worn.

8. The diaper of claim 1, wherein the channel in each of the pair of outer gussets is formed between an interior panel and an exterior panel of the diaper.

9. The diaper of claim 8, wherein the channel of each of the pair of outer gussets is formed using a seam along a periphery of the diaper at which the interior panel and the exterior panel are sewn together and a seam offset from the periphery of the diaper at which the interior panel and the exterior panel are sewn together.

10. A diaper comprising:
    a forward waist portion;
    a rearward waist portion;
    an intermediate portion between the forward waist portion and the rearward waist portion;
    a sealing apparatus including
       a pair of inner gussets each including a channel,
       a pair of outer gussets each including a channel,
       a single elastic member passing through the respective channels in each of the pair of outer gussets and each of the pair of inner gussets, and
    one or more adjustment mechanisms configured to adjust a tension of the single elastic member.

11. The diaper of claim 10, wherein the pair of outer gussets and formed along a periphery of the intermediate portion of the diaper.

12. The diaper of claim 11, wherein the first inner gusset and the first outer gusset fit around a first leg of a wearer and the second inner gusset and the second outer gusset fit around a second leg of a wearer when the diaper is worn.

* * * * *